United States Patent
Gomm et al.

(10) Patent No.: US 6,460,402 B1
(45) Date of Patent: Oct. 8, 2002

(54) ULTRASONIC FLUID QUALITY SENSOR SYSTEM

(75) Inventors: Tyler J. Gomm, Meridian, ID (US);
Nancy C. Kraft, Idaho Falls, ID (US);
Larry D. Phelps, Pocatello, ID (US);
Steven C. Taylor, Idaho Falls, ID (US)

(73) Assignee: Bechtel BWTX Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/496,788

(22) Filed: Feb. 2, 2000

Related U.S. Application Data

(60) Provisional application No. 60/118,561, filed on Feb. 4, 1999.

(51) Int. Cl.[7] .............................................. G01N 29/02
(52) U.S. Cl. ............................. 73/24.01; 73/861.04
(58) Field of Search .................... 73/570, 597, 600, 73/602, 609, 610, 614, 620, 861.28, 590, 592, 622, 24.01, 24.02, 24.03, 24.06, 861.04

(56) References Cited

U.S. PATENT DOCUMENTS

| | | | |
|---|---|---|---|
| 3,648,513 A | 3/1972 | Patterson ........................ 73/53 |
| 3,651,687 A | * 3/1972 | Dory ............................ 73/596 |
| 3,697,936 A | 10/1972 | Zacharias, Jr. et al. .......... 340/3 |
| 3,834,806 A | 9/1974 | Whited ............................ 355/3 |
| 3,914,999 A | * 10/1975 | Grandchamp ............ 73/861.25 |
| 3,981,176 A | 9/1976 | Jacobs .............................. 73/24 |
| 4,003,242 A | 1/1977 | Houben et al. ................. 73/24 |
| 4,095,457 A | 6/1978 | Koda et al. ...................... 73/53 |
| 4,117,716 A | 10/1978 | Simon ............................ 73/32 |
| 4,173,898 A | * 11/1979 | Forstermann et al. .......... 73/611 |
| 4,220,404 A | 9/1980 | Noguchi et al. ................. 73/24 |
| 4,246,773 A | 1/1981 | Haruta ............................ 73/24 |
| 4,246,993 A | 1/1981 | Morscheck .................. 192/53 |
| 4,308,519 A | 12/1981 | Garcea et al. ................. 340/53 |
| 4,313,343 A | 2/1982 | Kobayashi et al. ............ 73/290 |
| 4,314,242 A | 2/1982 | Kuru et al. ................. 340/617 |
| 4,331,025 A | 5/1982 | Ord, Jr. ............................ 73/54 |
| 4,357,918 A | 11/1982 | Asano ........................ 123/425 |
| 4,380,167 A | 4/1983 | Longini .......................... 73/24 |
| 4,424,702 A | 1/1984 | Schoenewolf .................. 73/24 |
| 4,463,729 A | 8/1984 | Bullis et al. ................. 123/478 |
| 4,465,046 A | 8/1984 | May ............................ 123/425 |
| 4,488,528 A | 12/1984 | Morikawa .................... 123/425 |
| 4,520,654 A | 6/1985 | Terhune .......................... 73/24 |
| 4,524,745 A | 6/1985 | Tominari et al. ........... 123/478 |
| 4,535,740 A | 8/1985 | Ma ............................ 123/435 |
| 4,555,932 A | 12/1985 | Crosby, Jr. ..................... 73/24 |
| 4,557,236 A | 12/1985 | Showalter .................... 123/435 |
| 4,576,047 A | 3/1986 | Lauer et al. ................... 73/597 |
| 4,896,133 A | 6/1986 | Smalling et al. ............... 73/24 |
| 4,646,522 A | 3/1987 | Mamiya et al. ............... 60/602 |
| 4,656,864 A | 4/1987 | Kraus et al. .................... 73/24 |
| 4,662,212 A | 5/1987 | Noguchi et al. ............... 73/24 |
| 4,665,737 A | 5/1987 | Britsch et al. ................. 73/35 |
| 4,724,812 A | 2/1988 | Akagi ........................ 123/435 |
| 4,845,976 A | 7/1989 | Johnson et al. ................ 73/23 |
| 4,887,575 A | 12/1989 | Takahashi .................... 123/435 |
| 4,962,739 A | 10/1990 | Wataya ........................ 123/435 |
| 5,036,669 A | 8/1991 | Earleson et al. .............. 60/602 |
| 5,060,507 A | 10/1991 | Urmson et al. ............ 73/24.01 |
| 5,060,514 A | 10/1991 | Alysworth ................. 73/24.01 |
| 5,131,224 A | 7/1992 | Siewert et al. ................ 60/274 |
| 5,247,826 A | 9/1993 | Frola et al. ................. 73/24.01 |
| 5,285,675 A | 2/1994 | Colgate et al. .............. 73/23.2 |

(List continued on next page.)

*Primary Examiner*—Helen Kwok
(74) *Attorney, Agent, or Firm*—Workman Nydegger & Seeley

(57) ABSTRACT

A system for determining the composition of a multiple-component fluid and for determining linear flow comprising at least one sing-around circuit that determines the velocity of a signal in the multiple-component fluid and that is correlatable to a database for the multiple-component fluid. A system for determining flow uses two of the inventive circuits, one of which is set at an angle that is not perpendicular to the direction of flow.

61 Claims, 2 Drawing Sheets

U.S. PATENT DOCUMENTS

| | | |
|---|---|---|
| 5,285,677 A | 2/1994 | Gehler ........................ 73/24.01 |
| 5,313,820 A | 5/1994 | Aylsworth .................. 73/24.01 |
| 5,325,703 A | 7/1994 | Magori ....................... 73/23.32 |
| 5,343,760 A | 9/1994 | Sultan et al. ............. 73/861.04 |
| 5,351,522 A | 10/1994 | Lurat ........................ 73/24.01 |
| 5,353,627 A | 10/1994 | Diatschenko et al. ...... 73/19.03 |
| 5,369,979 A | 12/1994 | Aylsworth et al. .......... 73/24.01 |
| 5,392,635 A | 2/1995 | Cadet et al. ................ 73/24.01 |
| 5,467,637 A | 11/1995 | Hasegawa et al. .......... 73/24.01 |
| 5,503,035 A * | 4/1996 | Itoh et al. ................. 73/861.23 |
| 5,537,854 A | 7/1996 | Phillips et al. ............. 73/24.01 |
| 5,627,323 A | 5/1997 | Stern ........................ 73/861.28 |

* cited by examiner

ULTRASONIC FLUID QUALITY SENSOR SYSTEM

RELATED APPLICATIONS

This application claims priority to U.S. patent application Ser. No. 60/118,561 filed on Feb. 4, 1999 and is incorporated herein by specific reference.

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

1. Field of the Invention

The present invention relates to a system for the quantitative analysis of a fluid that has known components. More particularly, the present invention relates to a system for measuring acoustic pulses in the multiple-component fluid. In particular, the present invention relates to a velocimeter and a method of applying acoustic transmission delay data to empirical correlations with the multiple-component gases.

2. Relevant Technology

Many fluid flow applications require real-time evaluation for various reasons such as fluid quality evaluation. and process control. Such real-time evaluation is only complicated where the fluid is a mixture of multiple components. For applications such as in the natural gas industry for gas-fired systems, or in the carburation of a fuel mixture for an internal combustion engine, operating parameters may critically depend upon the ratio of fluid components in relation to each other. Where a correlation exists for known ratios between multiple components and a given parameter of a particular mixture, such a correlation may be used to facilitate an optimal process that uses the mixture.

One example of the need for real-time evaluation is with natural gas internal combustion engines. Natural gas may have a methane content in a range from about 75% to about 99% methane. This methane composition range can vary between different sources and also the life of the source and the time of year in which the natural gas is removed from the source. Engine knocking is the phenomenon of a pre-ignition of the fuel in the combustion chamber. Knocking has a detrimental and often destructive effect upon the internal combustion engine combustion chamber. It is important therefore in this example of the need for real-time evaluation, to allow an internal combustion engine to be reconfigured in its combustion cycle depending upon the quality of the natural gas that is being supplied.

A well-understood correlation that can be applied to a given process may have a wide variety of applications. Examples thereof include the above-mentioned applications and others such as in the paper and pulp industry, the textile industry, the petroleum industry, materials and chemical testing, effluent monitoring, environmental discharge monitoring, and fluid commodity delivery. All of these applications could all be greatly affected by such a system.

Various problems and challenges occur depending upon the selected multiple-component fluid. For example, gaseous systems have been limited to conventionally lower frequencies because of the extreme attenuation of a high frequency audio signal in the gaseous system. Another difficulty occurs in a gaseous system where the particular geometry confines the distance between a transmitter and a receiver to close proximity. In such a system, there tends to be capacitative coupling between the transmitter and receiver. A capacitative coupling tends to generate a spurious signal that can be misinterpreted by the system as a response signal from the generated acoustic signal.

Another problem occurs where such systems are used around other equipment and machinery. In such an environment, electromagnetic and acoustic noise may be generated at frequencies that are similar to those designed to be detected in the testing system.

What is needed in the art is a system for quantitatively estimating the make-up of a known multiple-component fluid that overcomes the problems of the prior art. What is needed is a system that overcomes such problems as the unavoidable spurious signal that is generated where capacitative coupling in a gaseous system due to the geometry of the system requires the transmitter and receiver transducers to be in close proximity to each other. What is needed in the art is a system that can operate at high frequencies such that a rapid response and adjustment to the multiple-component fluid can be made for optimal performance of a given process.

Such systems, methods, and apparatuses are disclosed and claimed herein.

SUMMARY AND OBJECTS OF THE INVENTION

The present invention relates to a system for quantitatively determining the components of a known multiple-component fluid.

In one embodiment of the invention, the system uses a "sing-around" circuit that filters out capacitative coupling in a gaseous system. In this embodiment of the present invention, a high-frequency audio signal is generated from a transmitter and detected by a receiver. A high frequency audio signal experiences extreme attenuation in a gaseous system. However, a portion of the audio signal reaches the receiving transducer. The audio signal is converted into an electronic signal that is sent to a triggering system. Due to the extreme attenuation of the audio signal, the electronic signal must be boosted by an amplification circuit sufficient to create a triggering signal.

In the triggering system, the electronic signal is amplified to assist in overcoming the extreme attenuation of the audio signal. Following amplification, the signal is rectified and gathered into a substantially half wave form. Spurious signals that are generated due to capacitative coupling and other causes are filtered out by a gate or digital filter. The digital filter is tuned to anticipate approximately the time period when actual signals should pass therethrough and the digital filter simply eliminates any other signals that come outside the anticipated signal time window. Following digital filtration, the wave form is converted into a square wave and optionally changed in pulse width to optimize it as a triggering signal. The triggering signal is then ultimately sent to a pulser that instructs the transmitter to generate another audio signal.

A "keep-alive" circuit is also provided in the sing-around loop for the occasion where no signal is detected to be cycling within the loop. The keep-alive circuit is configured to look for a pulse coming from upstream in the circuit loop. It looks for a pulse of a particular waveform, namely the square wave, and of a particular pulse width that is characteristic of that which was made of the circuit following digital filtration and conversion into a square wave. Where the anticipated signal is not received within a particular time window, the "keep alive" circuit generates its own signal, directed to the pulser, that instructs the transmitter to generate another audio signal in the direction of the receiver.

In any event, a pulse signal is generated and directed to the transmitter. At this point, a new audio signal is generated from the transmitter and detected by the receiver. After a number of cycles, the "sing-around" circuit settles down to its designed cycling time. The amount of time required to relay the signal from the receiver around to the transmitter is known. The largest time lapse in the circuit is the time required for the audio signal to bridge the distance between the transmitter and the receiver. As such, the speed of sound in the known multiple-component fluid can be extracted from the total cycling time of the circuit.

As the components of the multiple-component fluid are known, a database comprising the speed of sound at various component ratios of the known multiple-component fluid may be referred to and an estimate of the precise composition of the multiple-component fluid may be made. The simplest systems comprise binary, or two-component fluids. Two-component fluids generally have a linear or simple non-linear relationship such as the speed of sound as a function of concentration of the two components in the fluid.

Where the multiple-component fluid is a ternary system, a quaternary system, or greater, additional properties of the multiple-component fluid may need to be tested for determination of the ratios of the individual components. Examples of additional properties may include heat capacity, electrical conductivity, spectroscopic qualities such as nuclear magnetic resonance, infrared, and others, and optical qualities such as fluid color and index of refraction. Where a multiple-component fluid is being used in a dynamic system that requires a frequent reevaluation of the makeup of the system or greater, preferred tests will be those that have a rapid-evaluation time that is sufficient for the system to be adjusted to optimize operation thereof with the particular multiple-component fluid flowing through it.

It is therefore an object of an embodiment of the present invention to provide a system that overcomes the problems of the prior art. It is also an object of an embodiment of the present invention to provide a system for the evaluation of the quality of a multiple-component fluid as it relates to its usefulness as a fluid commodity.

It is also an object of an embodiment of the present invention to provide a sing-around circuit to evaluate a gaseous fluid that filters all spurious signals.

It is also an object of an embodiment of the present invention to provide a system for the evaluation of a multiple-component fluid that is being used in a dynamic system. It is also an object of an embodiment of the present invention to provide a system for the measurement and control of fluid flow that is being conveyed in a conduit.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to a system for quantitatively determining the components of a known multiple-component fluid. It is assumed throughout this disclosure that uniform fluid flow in a conduit is being analyzed. However, flow may comprise single-phase or multiple phase laminar or turbulent plug flow, and multiple-phase flow. Preferably the flow regime is single-phase flow.

In a first embodiment of the present invention, the problem of capacitative coupling and its production of a spurious signal is overcome with the inventive system. In some geometries, placement of the transmitter and the receiver must be in such a close proximity that in a gaseous system, the transmitter and the receiver act as capacitor plates. The size of the capacitative charge between two plates is dependent upon the exposed surface areas and the distance therebetween.

Figure 1A:
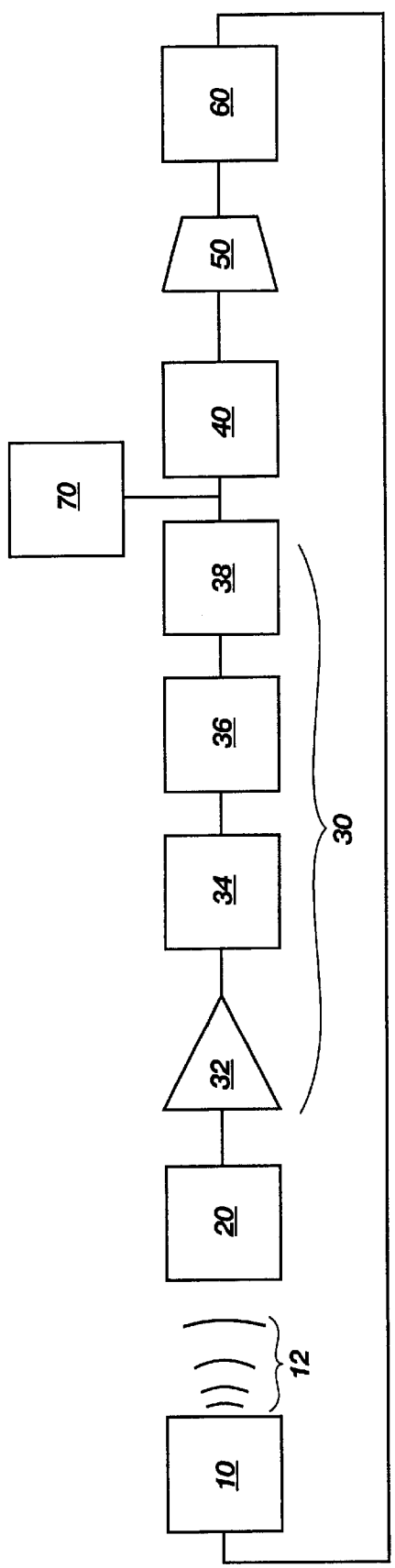
FIG. 1a is a block diagram of a sing-around circuit that is part of the inventive system.
Figure 1B:
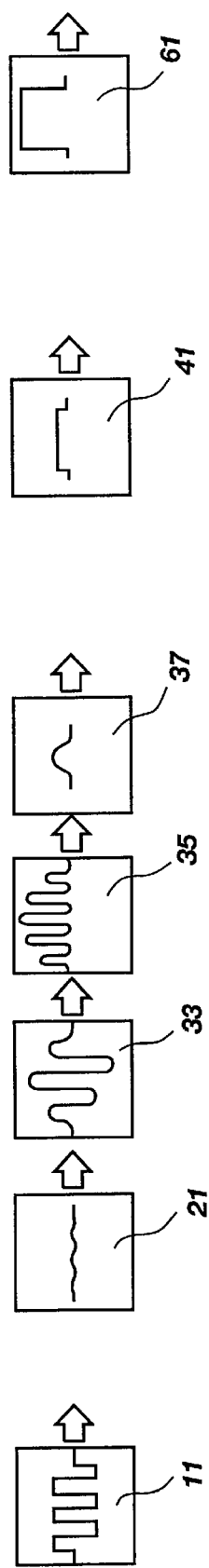
FIG. 1b is an illustration of the inventive signal processing that corresponds to the sing-around circuit of the present invention.

FIG. 1a is a block diagram illustration of the inventive system. FIG. 1b further illustrates the inventive system by illuminating the signal that is being manipulated. The block diagrams in FIG. 1b that are positioned immediately beneath the block diagrams in FIG. 1a, illustrate the signal as processed in the respective block diagrams of FIG. 1a.

A transmitter 10 generates an audio signal 12 of waveform 11 that is broadcast in the direction of a receiver 20. Audio signal 12 moves through a medium between transmitter 10 and receiver 20. Typically, the medium is a solid, a liquid, or a gas; preferably it is a gas. Receiver 20 detects audio signal 12 and an electronic signal is generated within receiver 20 as illustrated in FIG. 1b.

The remainder of the inventive system is a means for determining the signal delay between the transmitter and the receiver. The inventive system includes a high frequency signal as defined below, propagating through a gaseous medium, and the configuration of a trigger circuit 30 that overcomes the problems of the prior art.

The signal is transmitted to an amplifier 32 in order to overcome the likely extreme attenuation of the broadcast signal that occurs between transmitter 10 and receiver 20.

Amplified signal 33 is then transmitted to a rectifier 34 to substantially eliminate the sinusoidal nature thereof. A rectified signal 35 is then transmitted to an envelope detection circuit 36 that converts rectified signal 35 into a half wave 37. Half wave 37 is then transmitted to a masking or gate circuit. The masking or gate circuit acts as a digital filter. The inventive system is configured to expect reception of half wave 37 at digital filter 38 within a certain time window. All spurious signals that arrive at digital filter 38 outside the time window, are substantially eliminated thereby. Following the digital filtration of half wave 37, the signal is transmitted to a pulse width adjuster 40. Pulse width adjuster 40 is placed within the inventive system to provide an adequate triggering signal to cause transmitter 10 to repeat its transmission to receiver 20. Typically, the pulse width of half wave 37 will be inadequate, namely too narrow, to facilitate the triggering of a new pulse from transmitter 10. Therefore, a TTL or square wave 41 is generated at pulse width adjuster 40.

The inventive system also uses a "keep-alive" circuit 50 that is configured to send a square wave approximately equivalent to square wave 41 to a pulser 60. Pulser 60 receives either square wave 41 from pulse width adjuster 40 or a similar square wave from keep alive circuit 50. Pulser 60 then in turn generates a signal that induces transmitter 10 to repeat the cycle.

A digital readout 70 is placed somewhere after digital filter 38 in order to provide an observer with information regarding the cycling time of the inventive system. Digital readout 70 may be configured to display a frequency of the total cycling time of the inventive system. The total cycling time of the inventive system is correlatable to different fluid compositions and the respective speeds of sound therein. Digital readout 70 may display a cycling time frequency that, depending upon the medium being tested, will allow the observer to compare the frequency to known binary fluid systems and to arrive at an estimated composition ratio of the components thereof. Alternatively, digital readout 70 may simply relay its information to another system that assists to correlate the fluid's audio transmission characteristics to its composition ratio.

After employment of the means for determining the signal delay between the transmitter and the receiver, a means for correlating the signal delay to a database is employed for the multiple-component fluid. In its simplest form, the means for correlating the signal delay to a database includes the decision whether to eliminate the signal processing time between receiver 20 and transmitter 10 from the total cycling time of the inventive circuit or whether to ignore it. Another portion of the means for determining the signal delay between the transmitter and the receiver includes empirical data and digital readout 70.

In a specific embodiment of the present invention, transmitter 10 and receiver 20 are separated by a distance of less than about 10 cm. In this embodiment of the present invention, transmitter 10 and receiver 20 may be spaced apart in a range from about 0.5 cm to about 20 cm and the exposed surface area of each that acts as a capacitative plate is in a range from about 1 $cm^2$ to about 20 $cm^2$. The surface area of each exposed portion thereof that acts as a capacitor is preferably less than about 10 $cm^2$. Capacitance may be created between the two surfaces of transmitter 10 and receiver 20 that are exposed. The creation of a capacitative coupling therebetween is proportional to both the exposed surface area and to the magnitude of the capacitative charge. The placement of transmitter 10 and receiver 20 in much closer quarters such as a 5 cm separation, a 2 cm separation or a 1 cm separation, even with a smaller exposed surface area therebetween will cause capacitative coupling to occur along with its spurious signal generation.

An example of this application of the present invention is in the carburation of a fuel mixture for an internal combustion engine or in determining the quality of natural gas in a pipeline where the capacitative coupling effect occurs due to both the magnitude of the capacitative charge and the surface areas of transmitter 10 and receiver 20 that are exposed. Transmitter 10 generates a signal in a frequency range between about 100 kHz to about 10 MHz. In this application, where audio signal 12 is transmitted through a gas, attenuation thereof is extreme due to high frequencies. A frequency for a gaseous system is in a range from about 500 KHz to about 5 MHz, preferably about 1 MHz. At this frequency range, attenuation may exceed 50%, may exceed 90%, and may exceed 99.9%.

In order to avoid sending a spurious signal generated by capacitative coupling substantially simultaneously with audio signal 12, audio signal is generated in a pulse width in a range of about 0.1 microseconds to about 5 microseconds. Preferably, the pulse width is in a range from about 1 microsecond to about 3 microseconds, and more preferably about 2 microseconds. Due to the extreme narrowness of the pulse width of audio signal 12, and due to the extreme attenuation of such a high frequency signal in a gaseous medium, reception thereof by receiver 20 is problematic. As such, received signal 21 is amplified in amplifier 32 for a gain between about 100 and about 10,000, preferably 200 and 5,000, and most preferably about 1,000. A variable-gain amplifier may be used to tune the inventive system such that received signal 21 is amplified sufficiently to be further processible. In the gaseous system, the size of the gain in amplifier 32 is generally configured to be directly proportional to the frequency of the audio signal. In this embodiment, the gain is about 1,000, the frequency is about 1 MHz, and the pulse width is about 2 microseconds.

Following the conversion of received signal 21 into amplified signal 33, amplified signal 33 is converted into rectified signal 35. Thereafter, rectified signal 35 is manipulated into a half wave form, into a half wave 37, and directed further. Half wave 37, whether a spurious signal or a desired signal, is directed though digital filter 38.

As previously explained, a time window during which the desired signal is received is closed to all other signals such as a signal generated due to capacitative coupling between transmitter 10 and receiver 20. Typically, because the pulse width is about 2 microseconds wide, pulse width adjuster 40 is provided to make half wave 37 into square wave 41. Pulse width adjuster 40 is capable of both diminishing the size of half wave 37 or increasing the its size. Typically, the pulse width is about 2 microseconds and pulse width adjuster 40 adjusts the size of half wave 37 to be approximately 10 microseconds wide. The advantage to making the pulse width approximately 10 microseconds wide is that the circuit does not accidently trigger more than once within a preferred time period.

Square wave 41 passes further through the circuit to keep-alive circuit 50. Keep-alive circuit 50 waits for a preferred time period to receive a detected signal and if no signal is received, keep-alive circuit 50 generates its own signal to pulser 60 in order to repeat generation of audio signal 12. In this embodiment, the timing window, or waiting time, is between about 50 and 500 microseconds, preferably about 100 and about 300 microseconds, and most preferably about 200 microseconds.

Square wave 41 or a square wave from keep alive circuit 50 is generated. In any event, a square wave of about 10 microseconds width enters pulser 60 and is of sufficient voltage, amplitude and duration to cause transmitter 10 to repeat the transmission of audio signal 12.

The time delay between the transmission of audio signal 12 and the reception thereof at receiver 20 is-significantly larger than all other elapsed time within the circuitry of the inventive system. As such, the elapsed time to process received signal 21 as a part of the entire cycling time of the inventive system may either be disregarded or subtracted. Subtraction of the signal processing time as part of the total elapsed time of each cycle becomes less important as the distance between transmitter 10 and receiver 20 increases. Pulser 60 generates a TTL square wave voltage spike 61 in a range from about 60 volts to about 220 volts, preferably about 120 volts. In response, transmitter 10 generates a signal that propagates to receiver 20.

Pulser 60 is designed to repeat pulses at a rate between about 10 to about 100 KHz, preferably between about 40 to about 50 KHz. In other words, elapsed time for one cycle between a first pulse and a second pulse is in this kilohertz range. The rate is dependent upon the speed of the audio signal as it propagates through the medium being tested and the distance between transmitter 10 and receiver 20.

Tests were run on the inventive system. For Test 1, the frequency of the circuit was determined in air and was found to be between 31.687 and 31.667 kHz.

The following tests were run on air and on He/N systems. In each test, the frequency was taken from digital readout 70. Tests 1 through 15 were taken a separation between transmitter 10 and receiver 20 of 1 cm. 1 cm herein is taken as equal to 0.3937 inches. Table 1 depicts Tests 2 through 16 for He/N systems.

TABLE 1

| Test No. | % He | Temp (degree F.) | Frequency (kHz) |
|---|---|---|---|
| Run 1 @ 1 cm | | | |
| 2 | 45 | 74.1 | 40.559 |
| 3 | 35 | 74.9 | 38.113 |
| 4 | 25 | 74.6 | 36.107 |
| 5 | 15 | 75.2 | 34.344 |
| 6 | 5 | 75 | 32.805 |
| Run 2 @ 1 cm | | | |
| 7 | 45 | 74.6 | 40.55 |
| 8 | 35 | 74.9 | 38.104 |
| 9 | 25 | 74.8 | 36.096 |
| 10 | 15 | 75.3 | 34.309 |
| 11 | 5 | 75.1 | 32.791 |
| Run 3 @ 1 cm | | | |
| 12 | 45 | 74.5 | 40.523 |
| 13 | 35 | 75 | 38.097 |
| 14 | 25 | 74.9 | 36.11 |
| 15 | 15 | 75.4 | 34.329 |
| 16 | 5 | 75.1 | 32.8 |

For Test 17, the frequency of the circuit was determined in air and was found to be between 16.564 and 16.498 kHz. Table 2 depicts Tests 18 through 32 for He/N systems.

TABLE 2

| Test No. | % He | Temp (degree F.) | Frequency (kHz) |
|---|---|---|---|
| Run 1 @ 2 cm | | | |
| 18 | 45 | 74.5 | 21.541 |
| 19 | 35 | 74.9 | 20.177 |
| 20 | 25 | 74.8 | 19.002 |
| 21 | 15 | 75 | 18.038 |
| 22 | 5 | 75.2 | 17.15 |

TABLE 2-continued

| Test No. | % He | Temp (degree F.) | Frequency (kHz) |
|---|---|---|---|
| Run 2 @ 2 cm | | | |
| 23 | 45 | 74.7 | 21.552 |
| 24 | 35 | 74.8 | 20.178 |
| 25 | 25 | 74.7 | 18.996 |
| 26 | 15 | 75 | 18.04 |
| 27 | 5 | 75.2 | 17.159 |
| Run 3 @ 2 cm | | | |
| 28 | 45 | 74.7 | 21.555 |
| 29 | 35 | 74.7 | 20.175 |
| 30 | 25 | 74.4 | 18.975 |
| 31 | 15 | 75.1 | 18.045 |
| 32 | 5 | 75.1 | 17.154 |

For Test 33, the frequency of the circuit was determined in air and was found to be between 11.200 and 11.186 kHz. Table 3 depicts Tests 34 through 48 for He/N systems.

TABLE 3

| Test No. | % He | Temp (degree F.) | Frequency (kHz) |
|---|---|---|---|
| Run 1 @ 3 cm | | | |
| 34 | 45 | 74.8 | 14.697 |
| 35 | 35 | 74.8 | 13.716 |
| 36 | 25 | 74.4 | 12.922 |
| 37 | 15 | 75.2 | 12.227 |
| 38 | 5 | 75.1 | 11.628 |
| Run 2 @ 3 cm | | | |
| 39 | 45 | 74.5 | 14.699 |
| 40 | 35 | 74.9 | 13.71 |
| 41 | 25 | 74.5 | 12.921 |
| 42 | 15 | 75.2 | 12.233 |
| 43 | 5 | 75.1 | 11.626 |
| Run 3 @ 3 cm | | | |
| 44 | 45 | 74.5 | 14.685 |
| 45 | 35 | 74.9 | 13.715 |
| 46 | 25 | 74.6 | 12.917 |
| 47 | 15 | 75.2 | 12.232 |
| 48 | 5 | 75.2 | 11.633 |

In all of examples 1 through 48, it was surprisingly discovered that the inventive system was capable of processing a high frequency audio signal in a gas where it was known that attenuation in a gas at the frequencies contemplated and used would be extreme and significant. Additionally, at the separation distance between transmitter 10 and receiver 20, the problem of capacitative coupling and its generation of a spurious signal was overcome by the conception and reduction to practice of digital filter 38. Data from Tests 1 through 48, in connection with the inventive system, provide a reliable correlation between the frequency of the sing-around circuit of the present invention and the gas systems tested. As such, the method for determining the composition of a multiple-component fluid was surprisingly successful in spite of the limitations known for such systems in the prior art.

Figure 2:
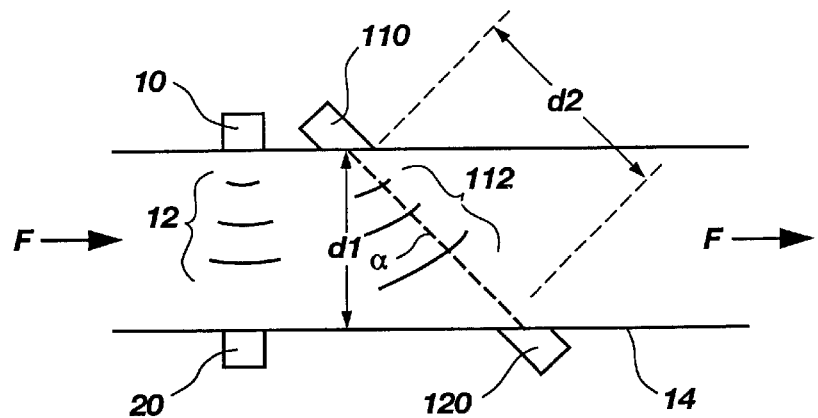
FIG. 2 is an elevational cross-section illustration of one embodiment of the present invention, wherein a pair of circuits evaluate both fluid composition and fluid flow rate.

In another embodiment of the present invention, the inventive system is used as a duplicate pair of circuits from which the linear flow of the fluid can be determined. FIG. 2 is an elevational cross-section view of this embodiment. It can be seen that transmitter 10 and receiver 20 are configured to transmit audio signal 12 substantially perpendicular to the direction of flow $V_f$ of a multiple-component fluid within a conduit 14. A second system is configured to transmit an oblique-angle audio signal 112 at an angle α, between a transmitter 110 and a receiver 120. Transmitter 10 and receiver 20 are used in conjunction with transmitter 110 and receiver 120 in order to assist to determine the linear flow rate of the fluid within conduit 14. The speed of audio signal 12 as it passes through the fluid is determined between transmitter 10 and receiver 20 as set forth above. Because the multiple-component fluid composition may be presumed to be substantially homogeneous within conduit 14 between transmitter 10 and receiver 20 and between 110 and receiver 120, and because the distances d and d are known, the angled configuration of transmitter 110 and receiver 120 in relation to the direction of flow $V_f$ will cause oblique audio signal 112 to reach receiver 120 earlier than anticipated by a factor of approximately the linear flow rate multiplied by the trigonometric cosine of the angle α. In the past, calculation of flow velocity by similar methods required dependency upon such variables as system pressure, system temperature, and the composition of the multiple-component fluid. With the inventive method, system pressure, system temperature, and system composition are substantially eliminated as data from the duplicate pair of circuits is compared. A distinct advantage exists in the inventive system where flow calculation is greatly simplified by the elimination of dependency upon the aforementioned variables. Thus, transmitter 10 and receiver 20 provide a baseline, known audio-signal speed in the multiple-component fluid composition. Transmitter 110 and receiver 120 along with the reception of oblique audio signal earlier than anticipated allows for the determination of linear flow within conduit 14. Preferably, angle α may be 45° or smaller. As angle α becomes smaller and approaches 0°, the accuracy of measuring linear flow may increase.

Figure 3:
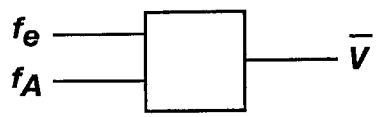
FIG. 3 is a block diagram that illustrates signal processing achieved in the embodiment depicted in FIG. 2.

FIG. 3 is a block diagram that illustrates signal processing achieved in the embodiment depicted in FIG. 2. As a means for calculating Doppler shift effect, $f_0$ and $f_1$ are used to arrive at the flow velocity, $V_f$.

The combination of transmitter 10 and receiver 20 in connection with transmitter 110 and receiver 120 allow for a dynamic control capability for a system wherein the quality of the fluid must be constantly reevaluated and adjustments made therefore in order to achieve optimum system operation. As an example thereof, a natural gas-fired system such as a gas burner for a boiler, a low $NO_x$ burner, a rotary kiln, a gas combustion turbine, or other systems is supplied with natural gas and the inventive system depicted in FIG. 2 comprising conduit 14 and transmitters 10,110 and receivers 20,120 are positioned before the gas combustion apparatus.

Figure 4:
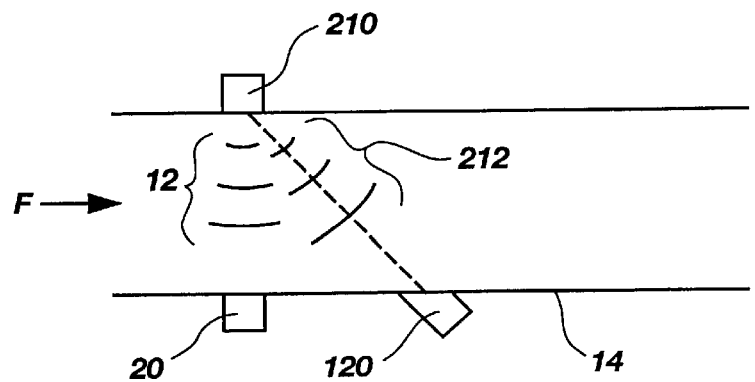
FIG. 4 is an illustration of an alternative embodiment of the device depicted in FIG. 2, wherein an integral transmitter generates a signal that can be detected by more than one receiver.

In an alternate embodiment, transmitter 10 and transmitter 110 are merged into an integral unit as transmitter 310, illustrated in FIG. 4. Receivers 320,420, 520,620 and 720 are multiplexed to accept audio signal 312. Audio signal 312 is broad enough to strike all receivers.

The following tests were conducted using the double sing-around circuit system of the present invention to calculate the flow rate of a known multiple-component fluid, namely He/N. Test 49 was conducted with air at about 73.2° F. Data from tests 1, 17, and 32 were used to correlate with Test 49. Air was passed through conduit 14 at a known rate of 20 cuft/hr. Separation between transmitter 10 and receiver 20 was about 1.695 inches. The inventive system settled down to a cycling frequency of about 7.833 kHz from which it was determined that oblique-angle audio signal 112 was carried forward to receiver 120 at a rate of about 0.0135 inches per microsecond. By use of a simple trigonometric calculation, the flow rate was found to be about 20 ft$^3$/hr.

Tests 50 through 61 were conducted using helium and nitrogen. The gas flow rate was derived from the data in a manner similar to that for the air flow rate Test 49.

| Test No. | Gas | Thermocouple Reading (deg. F.) | Frequency (kHz) | Gas Flow Rate (CFH) |
|---|---|---|---|---|
| | | Run 1 | | |
| 50 | 45% He/55% N | 73 | 10.321 | 20 |
| 51 | 35% He/65% N | 73 | 9.628 | 20 |
| 52 | 25% He/75% N | 73 | 9.062 | 20 |
| 53 | 15% He/85% N | 74 | 8.565 | 20 |
| 54 | 5% He/95% N | 74 | 8.131 | 20 |
| | | Run 2 | | |
| 55 | 45% He/55% N | 73 | 10.331 | 20 |
| 56 | 35% He/65% N | 73 | 9.629 | 20 |
| 57 | 25% He/75% N | 73 | 9.058 | 20 |
| 58 | 15% He/85% N | 73 | 8.561 | 20 |
| 59 | 5% He/95% N | 73 | 8.128 | 20 |
| | | Run 3 | | |
| 60 | 45% He/55% N | 73.2 | 10.333 | 20 |
| 61 | 45% He/55% N | 73.5 | 10.335 to 10.341 | 140 |

Test 61 was carried out at a substantially higher flow rate.

Because the components of the multiple-component fluid are known, and because correlations may be on hand that describe the multiple-component fluids and their quantitative component ratios, the overall flow rate of the gas and a "snap shot" of its quality may be determined with the inventive system in order to optimize the device that uses natural gas combustion. Additionally, where combustion product effluents must be monitored for environmental reasons, gas quality such as a high sulfur content may allow a combustion system to be adjusted in order to minimize the release of undesirable pollutants to the atmosphere.

Distinct advantages exist with the present invention. Evaluation of a multiple-component gas by the inventive method and system is essentially non-intrusive into a container such as conduit 14. Additionally, the "sing-around" circuitry for use in a gaseous system with an audio signal in the megahertz range allows for error band detection. At a high frequency, the error band does not change substantially if at all such that the inventive system may be used by broadcasting a range of frequencies at different times and any errors or time delays will remain consistent.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

We claim:

1. A method for determining the composition of a multiple-component fluid, comprising:
   providing a transmitter and a receiver, separated by a fixed distance, and with a fluid therebetween;
   transmitting a first pulse from said transmitter;
   receiving said first pulse across said fixed distance to create a receiver signal;
   creating a square wave trigger signal by;
   amplifying said receiver signal to create an amplified signal;
   rectifying said amplified signal to create a rectified signal;
   converting said rectified signal into a square wave trigger signal; and alternatively adjusting the width of said square wave trigger signal;

receiving said square wave trigger signal;

preventing further travel of said square wave trigger signal if said square wave trigger signal is received outside of a predetermined time window;

using said square wave trigger signal to transmit a second pulse from said transmitter;

determining a signal delay between transmitting and receiving; and correlating said signal delay to a data base for said multiple-component fluid.

2. A method for determining the composition of multiple-component fluid according to claim 1, wherein said first pulse and said second pulse are audio signals.

3. A method for determining the composition of multiple-component fluid according to claim 1, wherein said fluid is in a vaporous state.

4. A method for determining the composition of a multiple-component fluid according to claim 1, wherein said transmitter and said receiver each have an exposed surface area in a range from about 1 cm$^2$ to about 20 cm$^2$, and said exposed surface areas are separated by a distance in a range from about 0.5 cm to about 20 cm.

5. A method for determining the composition of a multiple-component fluid according to claim 1, wherein said first pulse is an audio signal in a frequency range from about 100 kHz to about 10 MHz.

6. A method for determining the composition of a multiple-component fluid according to claim 1, wherein said first pulse is an audio signal with a frequency of about 1 MHz.

7. A method for determining the composition of a multiple-component fluid according to claim 1, wherein at least one of said first pulse and said second pulse is an audio signal with an attenuation between said transmitter and said receiver in excess of about 50%.

8. A method for determining the composition of a multiple-component fluid according to claim 1, wherein at least one of said first pulse and said second pulse has an initial pulse width in a range from about 0.1 microseconds to about 5 microseconds.

9. A method for determining the composition of a multiple-component fluid according to claim 1, wherein said receiver signal is amplified for a gain between about 100 and about 10,000.

10. A method for determining the composition of a multiple-component fluid according to claim 1, wherein said square wave trigger signal has a width of about 10 microseconds.

11. A method for determining the composition of a multiple-component fluid according to claim 1, further comprising, providing a keep-alive circuit between said receiver and said transmitter, said keep-alive circuit having a timing window in a range from about 50 to about 500 microseconds.

12. A method for determining the composition of a multiple-component fluid according to claim 1, wherein said second pulse is generated from a source that has a potential in a range from about 60 volts to about 220 volts.

13. A method for determining the composition of a multiple-component fluid according to claim 1, wherein elapsed time between said first pulse and said second pulse is measurable in a range from about 10 kHz to about 100 kHz.

14. A system for determining the composition of a multiple-component fluid, the system comprising:

a transmitter and a receiver separated by a fixed distance;

a trigger circuit at least indirectly connected to said transmitter and said receiver;

means for determining a signal delay between said transmitter and said receiver;

means for correlating said signal delay to a data base for the multiple-component fluid; and means for eliminating an errant signal between said transmitter and said receiver.

15. A system for determining the composition of a multiple-component fluid according to claim 14, wherein said means for eliminating an errant signal between said transmitter and said receiver is capable of eliminating an errant signal generated by capacitative coupling between said transmitter and said receiver.

16. A system for determining the composition of a multiple-component fluid according to claim 14, wherein said trigger circuit further comprises:

a signal amplifier connected to said receiver;

a signal rectifier connected to said signal amplifier;

a signal converter connected to said signal rectifier; and an alternative signal width adjuster connected to said signal converter.

17. A system for determining the composition of a multiple-component fluid according to claim 14, wherein said multiple-component fluid is a homogeneously mixed gas.

18. A system for determining the composition of a multiple-component fluid according to claim 14, wherein said transmitter and said receiver each have an exposed surface area in a range from about 1 cm$^2$ to about 20 cm$^2$, and said exposed surface areas are separated by a distance in a range from about 0.5 cm to about 20 cm.

19. A system for determining the composition of a multiple-component fluid according to claim 14, wherein said transmitter generates an audio signal in a frequency range from about 100 kHz to about 10 MHz.

20. A system for determining the composition of a multiple-component fluid according to claim 14, wherein said transmitter generates an audio signal with a frequency of about 1 MHz.

21. A system for determining the composition of a multiple-component fluid according to claim 14, wherein said multiple-component fluid is a gas and said transmitter generates an audio signal with an attenuation between said transmitter and said receiver in excess of about 50%.

22. A system for determining the composition of a multiple-component fluid according to claim 14, wherein said transmitter generates a pulse with an initial pulse width in a range from about 0.1 microseconds to about 5 microseconds.

23. A system for determining the composition of a multiple-component fluid according to claim 14, wherein said trigger circuit has a signal amplifier with a gain between about 100 and about 10,000.

24. A system for determining the composition of a multiple-component fluid according to claim 14, wherein said trigger circuit generates a square wave signal with a width of about 10 microseconds.

25. A system for determining the composition of a multiple-component fluid according to claim 14, further comprising a keep-alive circuit disposed between said receiver and said transmitter, said keep-alive circuit having a timing window in a range from about 50 to about 500 microseconds.

26. A system for determining the composition of a multiple-component fluid according to claim 14, wherein said transmitter generates a second pulse having a potential in a range from about 60 volts to about 220 volts.

27. A system for determining the composition of a multiple-component fluid according to claim 14, wherein elapsed time for one cycling of said system is measurable in a range from about 10 kHz to about 100 kHz.

28. A system for determining the composition of a multiple-component fluid according to claim 14, further comprising means for eliminating an errant signal generated by capacitative coupling between said transmitter and said receiver, wherein said trigger circuit further comprises:

a signal amplifier connected to said receiver;

a signal rectified connected to said signal amplifier;

a signal converter connected to said signal rectifier; and a alternative signal width adjuster connected to said signal converter, wherein said multiple-component fluid is a homogeneously mixed gas, wherein said transmitter generates an audio signal in a frequency range from about 100 kHz to about 10 MHz, wherein said transmitter generates an audio signal with an attenuation between said transmitter and said receiver in excess of about 50%, wherein said transmitter generates a pulse with an initial pulse width in a range from about 0.1 microseconds to about 5 microseconds, wherein said signal amplifier has a gain between about 100 and about 10,000, wherein said trigger circuit generates a square wave signal with a width of about 10 microseconds, wherein said pulse has a potential in a range from about 60 volts to about 220 volts, and wherein elapsed time for one cycling of said system is measurable in a range from about 10 kHz to about 100 kHz.

29. A method of controlling a dynamic fluid-supply system comprising:

providing a first transmitter and a first receiver separated by first fixed distance and with a fluid therebetween;

transmitting a first pulse from said first transmitter;

receiving said first pulse across said first fixed distance to create a first receiver signal;

creating a first trigger signal;

using said first trigger signal to transmit a repeat pulse from said first transmitter;

determining a signal delay between transmitting and receiving of said first pulse;

providing a second transmitter and a second receiver, separated by a second fixed distance and with said fluid therebetween, wherein said second transmitter and said second receiver are configured at a non-perpendicular angle to flow of said fluid;

transmitting a second pulse from said second transmitter;

receiving said second pulse across said second fixed distance to create a second receiver signal;

creating a second trigger signal;

using said second trigger signal to transmit a repeat pulse from said second transmitter;

determining a signal delay between transmitting and receiving of said second pulse; and determining a transit-time shift between said second transmitter and said second receiver.

30. A method of controlling a dynamic fluid-supply system according to claim 29, wherein said first transmitter and said second transmitter are an integral unit.

31. A method of controlling a dynamic fluid-supply system according to claim 30, wherein transmitting both said first pulse and said second pulse comprises generating an audio signal in a frequency range from about 100 kHz to about 10 MHz, wherein said first pulse and said second pulse experience an attenuation between said first transmitter and said first receiver, and between said second transmitter and said second receiver, respectively, in excess of about 50%, wherein said first pulse and said second pulse each have an initial pulse width in a range from about 0.1 microseconds to about 5 microseconds, wherein each of said receiver signals is amplified for a gain between about 100 and about 10,000, wherein each of said receiver signals is converted into a square wave trigger signal with a width of about 10 microseconds, wherein said second pulse is generated from a source that has a potential in a range from about 60 volts to about 220 volts, and wherein elapsed time between said first pulse and second pulse is measurable in a range from about 10 kHz to about 100 kHz.

32. A method suitable for determining the composition of a multiple-component fluid, comprising:

transmitting a first pulse through the multiple-component fluid;

receiving said first pulse to create a receiver signal;

creating a trigger signal based upon said receiver signal;

receiving said trigger signal;

neutralizing said trigger signal if said trigger signal fails to conform with a predetermined criterion;

using said trigger signal, if not neutralized, to stimulate transmission of a second pulse;

determining a signal delay between transmitting and receiving of said first pulse; and using at least said signal delay to at least indirectly determine an identity of at least one component of the multiple-component fluid.

33. The method as recited in claim 32, wherein using said signal delay to at least indirectly determine an identity of at least one component of the multiple-component fluid comprises correlating said signal delay to a database for the multiple-component fluid.

34. The method as recited in claim 32, wherein creating a trigger signal comprises:

amplifying said receiver signal to create an amplified signal;

rectifying said amplified signal to create a rectified signal;

converting said rectified signal into a trigger signal, said trigger signal having a predetermined wave form; and alternatively adjusting the width of said predetermined wave form of said trigger signal.

35. The method as recited in claim 33, wherein said receiver signal is amplified for a gain between about one hundred (100) and about ten thousand (10,000).

36. The method as recited in claim 33, wherein said predetermined wave form comprises a square wave.

37. The method as recited in claim 36 wherein said trigger signal has a width of about ten (10) microseconds.

38. The method as recited in claim 32, wherein said trigger signal is neutralized when said trigger signal is not received within a predetermined time window.

39. The method as recited in claim 32, wherein correlation of said signal delay to a database for the multiple-component fluid is based upon a velocity of sound in the multiple-component fluid.

40. The method as recited in claim 32, wherein a frequency with which said trigger signal is generated corresponds to a characteristic of the multiple-component fluid.

41. The method as recited in claim 40, wherein said characteristic of the multiple-component fluid comprises a velocity of sound in the multiple-component fluid.

42. The method as recited in claim 32, wherein at least one of said first pulse and said second pulse comprises an audio signal.

43. The method as recited in claim 32, wherein at least one of said first pulse and said second has a frequency in a range of about one hundred (100) kHz to about ten (10) mHz.

44. The method as recited in claim 32, wherein said first pulse is attenuated in excess of about fifty (50) percent between transmission and reception.

45. The method as recited in claim 32, wherein at least one of said first pulse and said second pulse has an initial pulse width in a range of about one tenth (0.1) of a microsecond to about five (5) microseconds.

46. The method as recited in claim 32, wherein said second pulse has a potential in a range from about sixty (60) volts to about two hundred and twenty (220) volts.

47. The method as recited in claim 32, wherein an elapsed time between transmission of said first pulse and transmission of said second pulse is measurable in a range from about ten (10) kHz to about one hundred (100) kHz.

48. The method as recited in claim 32, further comprising neutralizing any trigger signals that are not based upon said receiver signal.

49. The method as recited in claim 48, wherein neutralizing any trigger signals that are not based upon said receiver signal comprises neutralizing at least those trigger signals whose generation results at least indirectly from capacitative coupling effects that occur in conjunction with performance of the method.

50. The method as recited in claim 32, further comprising transmitting said second pulse according to a predetermined criterion if said trigger signal is neutralized.

51. A system for determining the composition of a multiple-component fluid, the system comprising:
    a transmitter and a receiver separated by a fixed distance, at least a portion of said fixed distance being occupied by the multiple-component fluid;
    a trigger circuit;
    a gate circuit;
    a keep-alive circuit; and
    a data base for said multiple-component fluid,
wherein, said transmitter, receiver, trigger circuit, gate circuit, keep-alive circuit, and data base for said multiple-component fluid are in at least indirect communication with each other.

52. The system as recited in claim 51, wherein said transmitter, receiver, trigger circuit, and keep-alive circuit are connected in series.

53. The system as recited in claim 51, wherein said trigger circuit comprises a signal amplifier, a signal rectifier, a signal converter, and an alternative signal width adjuster.

54. The system as recited in claim 53, wherein at least said signal amplifier, signal rectifier, signal converter, and alternative signal width adjuster are connected in series.

55. The system as recited in claim 50, wherein said gate circuit comprises a digital filter.

56. The system as recited in claim 50, wherein said transmitter and said receiver each have an exposed surface area in a range from about 1 cm$^2$ to about 20 cm$^2$, and said exposed surface areas are separated by a distance in a range from about 0.5 cm to about 20 cm.

57. A method suitable for management of a multiple-component fluid flow, the method comprising:
    transmitting, from a first location, a first pulse through the multiple-component fluid; receiving said first pulse across to create a first receiver signal;
    creating a first trigger signal based upon said first receiver signal;
    using said first trigger signal to stimulate transmission of a repeat pulse;
    determining a first signal delay between transmitting and receiving of said first pulse;
    transmitting, from a second location, a second pulse;
    receiving said second pulse to create a second receiver signal;
    creating a second trigger signal based upon said second receiver signal;
    using said second trigger signal to stimulate transmission of a repeat pulse from said second location;
    determining a second signal delay between transmitting and receiving of said second pulse;
    determining a transit-time shift between said transmission and receipt of said second pulse; and
    adjusting at least one aspect of the multiple-component flow, based upon at least one of: said first signal delay, said second signal delay, and said transit time shift.

58. The method as recited in claim 57, wherein adjusting at least one aspect of the multiple-component flow comprises adjusting a quality of the multiple-component flow.

59. The method as recited in claim 57, further comprising determining a velocity of the multiple-component flow based upon at least one of: said first signal delay, said second signal delay, and said transit time shift.

60. The method as recited in claim 57, further comprising determining a mass flow rate of the multiple-component flow based upon at least one of: said first signal delay, said second signal delay, and said transit time shift.

61. The method as recited in claim 57, further comprising determining a quality of at least one component of the multiple-component flow based upon at least one of: said first signal delay, said second signal delay, and said transit time shift.

* * * * *